United States Patent [19]

Carlson

[11] 4,292,538
[45] Sep. 29, 1981

[54] SHAPED DETECTOR

[75] Inventor: Roland W. Carlson, Lyndhurst, Ohio

[73] Assignee: Technicare Corporation, Cleveland, Ohio

[21] Appl. No.: 64,835

[22] Filed: Aug. 8, 1979

[51] Int. Cl.³ .............................................. G01T 1/20
[52] U.S. Cl. ................................ 250/367; 250/445 T
[58] Field of Search ............ 250/361 R, 363 R, 363 S, 250/367, 369, 483, 368, 366, 486, 487

[56] References Cited

U.S. PATENT DOCUMENTS

| | | | |
|---|---|---|---|
| 3,225,193 | 12/1965 | Hilton et al. | 250/367 |
| 3,399,302 | 8/1968 | Carrell | 250/367 |
| 3,793,520 | 2/1974 | Grenier | 250/367 X |
| 3,944,833 | 3/1976 | Hounsfield | 250/367 |
| 4,037,105 | 7/1977 | Laurer | 250/367 |
| 4,039,839 | 8/1977 | Carlier | 250/483 |
| 4,070,581 | 1/1978 | Gibbons et al. | 250/445 T |
| 4,145,610 | 3/1979 | Perilhou | 250/367 |
| 4,159,424 | 6/1979 | Kingsley | 250/483 |
| 4,180,737 | 12/1979 | Kingsley | 250/367 |

OTHER PUBLICATIONS

Glover et al., "Theoretical Resolution of Computed Tomography Systems", Journal of Computer Assisted Tomography, vol. 3, No. 1, Feb. 1979.

*Primary Examiner*—Davis L. Willis
*Attorney, Agent, or Firm*—Fay & Sharpe

[57] ABSTRACT

A radiation detector or detector array which has a non-constant spatial response, is disclosed individually and in combination with a tomographic scanner. The detector has a first dimension which is oriented parallel to the plane of the scan circle in the scanner. Along the first dimension, the detector is most responsive to radiation received along a centered segment of the dimension and less responsive to radiation received along edge segments. This non-constant spatial response can be achieved in a detector comprised of a scintillation crystal and a photoelectric transducer. The scintillation crystal in one embodiment is composed of three crystals arranged in layers, with the center crystal having the greatest light conversion efficiency. In another embodiment, the crystal is covered with a reflective substance around the center segment and a less reflective substance around the remainder. In another embodiment, an optical coupling which transmits light from adjacent the center segment with the greatest intensity couples the scintillation crystal and the photoelectric transducer. In yet another embodiment, the photoelectric transducer comprises three photodiodes, one receiving light produced adjacent the central segment and the other two receiving light produced adjacent the edge segments. The outputs of the three photodiodes are combined with a differential amplifier.

55 Claims, 16 Drawing Figures

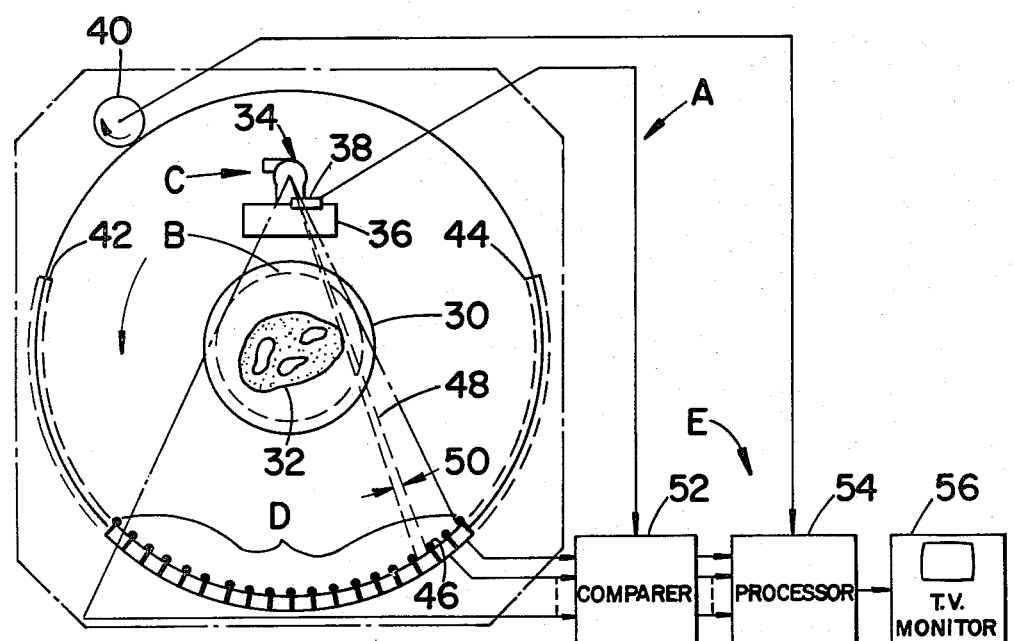
FIG. 1
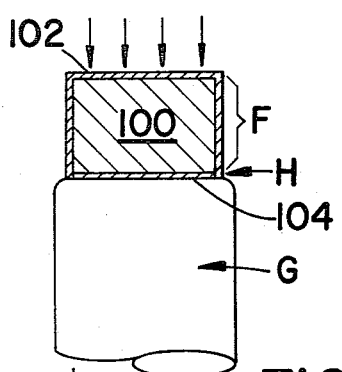
FIG. 2A
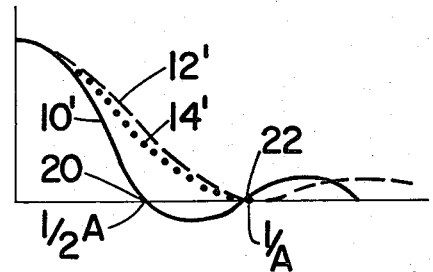
FIG. 3
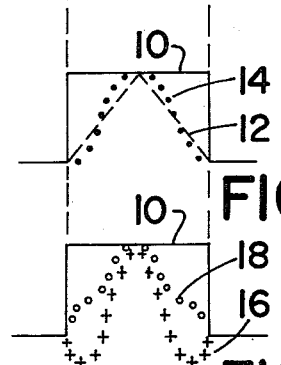
FIG. 2B
FIG. 2C
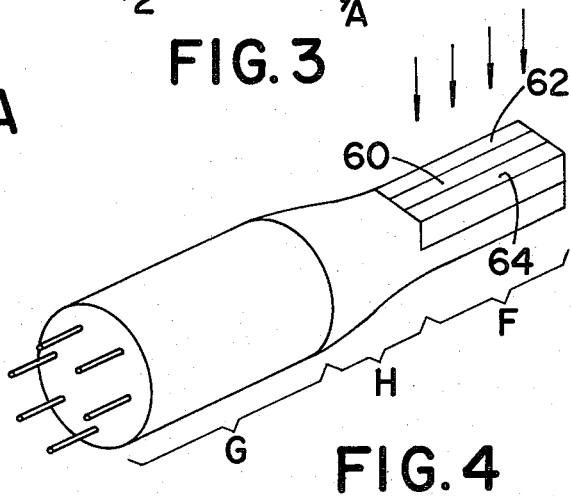
FIG. 4

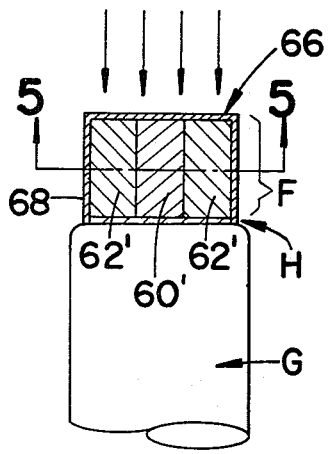
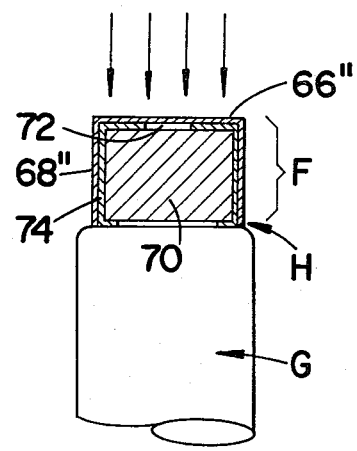
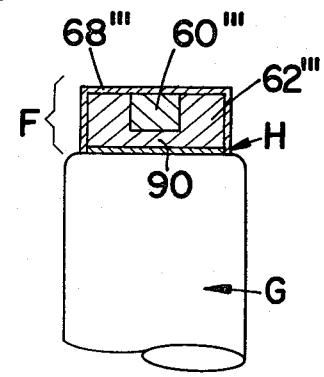
FIG. 5A　　　FIG. 6　　　FIG. 8
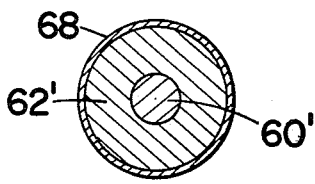
FIG. 5B
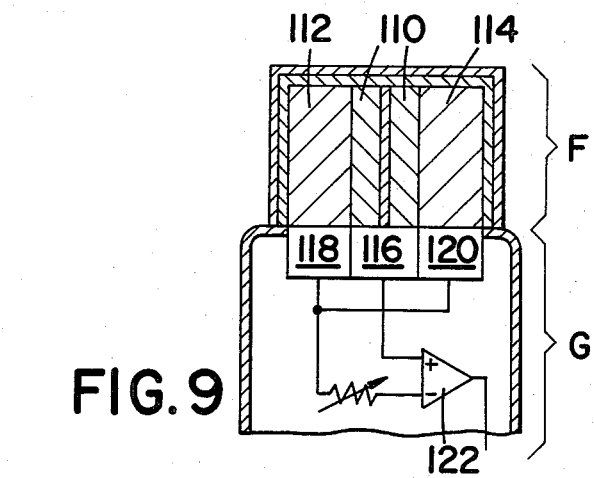
FIG. 9
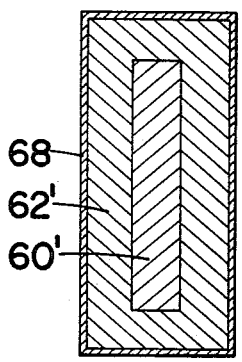
FIG. 5C
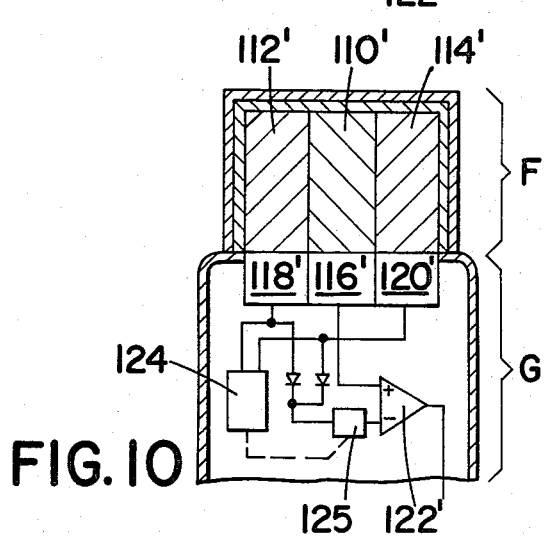
FIG. 10

SHAPED DETECTOR

BACKGROUND OF THE INVENTION

This application pertains to the art of radiant energy detection and more particularly, to apparatus for converting variations in incident, gamma or x-radiation into corresponding variations in an electrical property, such as changes in output voltage, current or resistance. The invention is particularly applicable to computerized axial tomographic scanners and will be described with particular reference thereto. It will be appreciated, however, that the invention has broader applications such as industrial flaw detectors and other apparatus which detect radiation with high resolution.

Generally, a computerized axial tomographic scanner comprises a source of radiation for irradiating a patient and a plurality of radiation detectors positioned opposite the patient from the radiation source. The detectors receive radiation beams which have passed through the patient along known paths. At least the radiation source is movably mounted for irradiating the patient from a plurality of directions. The detectors are positioned to detect the radiation beams along a plurality of intersecting paths through a planar slice of the patient. With well-known computer reconstruction techniques, the variation or attenuation of the radiation beams along the plurality of intersecting paths is reconstructed into an image of the planar region of the patient. The thickness of the beams along an axis generally transverse to the planar slice affects the thickness of the planar slice examined. The width of the beams affects the resolution of the reconstructed image. The width is an axis within the plane which is generally transverse to the thickness axis and transvierse to the path between the source and the detector. The radiation detectors generally consist of a scintillation crystal positioned to receive radiation and a photomultiplier tube optically coupled to the scintillation crystal. Alternately, the detectors may consist of a scintillation crystal optically coupled with a photodiode, a solid state radiation detector or an ionizable gas detector.

Generally, medical diagnosticians achieve the preferred results from tomographic scanners which have high resolution and low noise. A major factor in determining the resolution is the width of the radiation beams. The width may be determined by the width of the radiation receptive surface of the detector or by a source collimator. A scintillation crystal-photomultiplier tube detector generally has the scintillation crystal mounted in a support behind an aperture. The width of the aperture limits the width of the beam for reconstruction purposes. Additional radiation outside the beam which does not impinge on the receptive surface of the detector does not contribute to the reconstructed image even though it may pass through the patient.

Noise degrades the tomographic image. Generally, the amount of noise is related to the inverse square root of the number of photons of radiation received by the detector. Increasing the radiation receptive surface of the detector decreases the noise.

Accordingly, there is usually a trade-off between noise and resolution. Increasing the width of the radiation receptive surface of the detector reduces noise but also reduces resolution. Decreasing the width of the detector increases resolution but also increases noise.

The present invention contemplates a new and improved radiation detection apparatus which overcomes the above problems and others. The present invention contemplates a radiation detector which improves resolution without a corresponding increase in noise. Alternately, the present invention provides a detector that reduces noise without decreasing resolution.

SUMMARY OF THE INVENTION

One aspect of the invention is a radiation detector comprising a luminescence means for producing light in response to incident radiation and photoelectric means optically coupled with the luminescence means for producing electrical signals in response to light received from the luminescence means. The luminescence means has at least a first dimension comprised of at least a first segment and a second segment. The first and second segments of the luminescence means receive radiation and produce light. The photoelectric means is more responsive to the light produced in response to radiation received by the first segment than to the light produced in response to radiation received by the second segment. As a result, variations in the amount of radiation received adjacent the first segment will cause greater variations in the electrical signals than variations in the intensity of radiation received adjacent the second segment.

Another aspect of the invention is a radiation detector comprising a first scintillation crystal, a second scintillation crystal, and a photoelectric means optically coupled with the first and second scintillation crystals.

Another aspect of the present invention is a computerized tomographic scanning apparatus for examining a planar slice of an object in the plane of a scan circle with radiation and producing a representation of an image of the planar slice. The apparatus comprises a radiation source for producing at least one beam of radiation in the plane of the scan circle; a radiation detector means which has a non-constant spatial response along a first dimension in the plane of the beam for producing electrical signals in response to radiation received from the source that has traversed the scan circle; and a processing means for processing the electrical signals to produce the representation of an image.

A principal advantage of the invention is that it improves resolution without increasing noise. In a preferred embodiment of the invention, the spatial frequency response of the detector is twice that of a similar conventional detector while the noise is the same.

Another advantage of the invention is that it permits a reduction in noise or a decrease in radiation intensity over conventional detectors without degrading the limiting resolution.

BRIEF DESCRIPTION OF THE DRAWINGS

The invention may take physical form in certain parts and arrangements of parts, preferred and alternate embodiments of which all will be described in detail in this specification and illustrated in the accompanying drawings which form a part hereof.

FIG. 1 illustrates a tomographic scanner in accordance with the present invention;

FIG. 2A illustrates a radiation detector in accordance with the present invention;

FIGS. 2B and 2C illustrate spatial responses of detectors in accordance with the present invention;

FIG. 3 illustrates modulation transfer functions associated with the responses of FIGS. 2B and 2C;

FIG. 4 illustrates a preferred embodiment of a radiation detector in accordance with the present invention;

FIG. 5A illustrates a side section of an alternate embodiment of a radiation detector in accordance with the present invention;

FIG. 5B shows a preferred top section through section 5—5 of FIG. 5A;

FIG. 5C shows an alternate top section through sections 5—5 of FIG. 5A;

FIG. 6 illustrates a side section of an alternate embodiment of a radiation detector in accordance with the present invention;

FIG. 8 illustrates a side section of another embodiment of a radiation detector in accordance with the present invention;

FIG. 9 illustrates another alternate embodiment of a radiation detector in accordance with the present invention;

FIG. 10 illustrates another alternate embodiment of a radiation detector in accordance with the present invention;

DESCRIPTION OF THE PREFERRED EMBODIMENT

Figure 7:
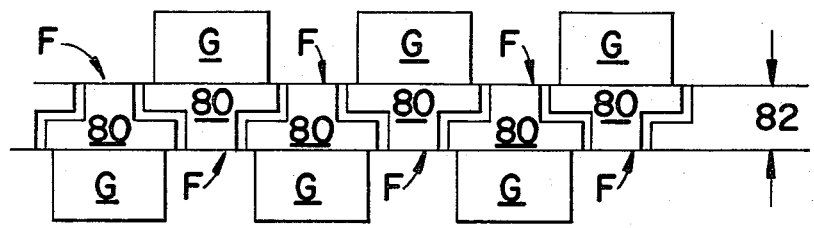
FIG. 7 illustrates a top plane view of a linear array of radiation detectors in accordance with the present invention.

Referring now to the drawings, the drawings are for the purpose of illustrating preferred embodiments of the invention only, and not for purposes of limiting the invention. The figures, note FIG. 1, show a computerized tomographic scanning apparatus A. A rotating fan beam type scanner is illustrated, however, the invention is also applicable to traverse and rotate and other types of scanners. The scanner includes a scan circle B which is adapted to receive a planar region of a patient to be examined. Adjacent the scan circle, is a rotatably mounted source of radiation C for irradiating the scan circle with a generally planar fan array of beams of radiation. Disposed opposite the scan circle from the source of radiation is a radiation detector means D. The radiation detector means has a non-constant or varying spatial response along a first dimension or width. The non-constant spatial response causes the detector means to weight the intensity of radiation received along a first more responsive segment of its width more heavily than radiation received along other less responsive segments. The detector means produces electrical signals indicative of the weighted sum or average of the amount of radiation received. As the source rotates, the radiation received by a detector traverses successive paths through the patient. The intensity of the radiation received varies with the coefficient of absorption of material along each path. This causes variations in the electrical signal. The variations in the amount of radiation received along the first, more heavily weighted segment of the width cause a correspondingly greater variation in the electrical signal than variations in the intensity of radiation received along less heavily weighted segments. A processing means E operates on the signals with algorithms well known in the tomographic art to produce a representation of the image of the planar region of the patient being examined.

In the preferred embodiment the detector means comprises a plurality of radiation detectors which have a non-constant spatial response along the first dimension or width. Each of the radiation detectors, note for example FIG. 2A, comprises a luminescence means F for transforming variations in incident radiation intensity into variations in light intensity. Optically coupled with luminescence means F is a photoelectric means G for receiving light from the luminescence means F and producing variations in an electrical signal in response to variations in the intensity of the received light. The detectors may further include an optical coupling means H for transmitting light from the luminescence means to the photoelectric means.

The present invention contemplates several embodiments in which one or more of the luminescence means F, photoelectric means G or optical coupling means H are designed to achieve the non-constant spatial response of the detector. Causing a non-constant response by partially blocking radiation from reaching the detector is undesirable because a patient is subject to radiation which is not used to produce the tomographic image. Rather than blocking radiation, the detector means or the detectors themselves produce a non-constant response. The beam of radiation from the source to a detector can be described in cross-section in terms of its thickness and its width. The spatial response of the detector of the present invention is described below in one dimension in terms of the response across the width of the detector. It will be appreciated that two and three dimensional non-constant spatial responses of the detectors are also included within the present invention as well as non-constant spatial responses in other directions, non-constant energy responses, and the like.

FIGS. 2B and 2C provide a graphic comparison of the spatial response of conventional detectors, curve 10, and the spatial response of detectors in accordance with the present invention, curves 12, 14, 16 and 18. The vertical axis of FIGS. 2B and 2C represents the magnitude of the response and the horizontal axis represents the spatial position along the width of the detector.

Response 10 may be described mathematically as:

$$f(x) = 1 \quad -A \leq x \leq A \quad (1)$$
$$= 0 \quad |x| > A$$

The spatial frequency response of the detector can be described in terms of a modulation transfer function (MTF). The modulation transfer function may be determined mathematically from the Fourier transform the response. The modulation transfer function of response 10 described by equation (1) is expressed as:

$$g(k) = 2 \int_0^A \cos(2\pi k x) dx = \frac{\sin(2A\pi k)}{\pi k} \quad (2)$$

The normalized modulation transfer function, which approaches unity as k becomes very small, is:

$$g_n(k) = \frac{\sin(2A\pi k)}{2A\pi k} \quad (3)$$

The modulation transfer function g(k) has zero amplitude at certain spatial frequencies. The first zero occurs at the spatial frequency $k_{01}$ which is found as follows:

$$g(k_{01}) = 0 = \sin(2A\pi k) = \sin(\pi) \quad (4)$$

Thus, the first zero of the spatial frequency $k_{01}$ is:

$$k_{01} = \tfrac{1}{2}A \tag{5}$$

The modulation transfer function of response 10 is illustrated by curve 10' of FIG. 3. The first zero, 20, in the spatial frequency is $\tfrac{1}{2}A$ units from the coordinate axis.

By appropriately constructing the luminescence means, optical coupling means, and photoelectric means, other spatial responses, as shown by curves 12, 14, 16 and 18, can be achieved. The generally triangular response, curve 12, can be expressed:

$$\begin{aligned} f(x) &= 1 - |x| & -A \le x \le A \\ &= 0 & |x| > A \end{aligned} \tag{6}$$

The normalized modulation transfer function of this curve can be shown to be:

$$g_n(k) = \left(\frac{\sin(A\pi k)}{A\pi k}\right)^2 \tag{7}$$

The first zero of the spatial frequency is:

$$k_{01} = 1/A \tag{8}$$

By comparing equations (5) and (8) above, it can be seen that the spatial frequency of the first zero for a generally triangular detector response is double the spatial frequency of a generally rectangular response. The modulation transfer function of curve 12 is illustrated graphically as curve 12' of FIG. 3. The first zero 22 of the spatial frequency of curve 12' is shown 1/A units from the coordinate axis. Doubling the spatial frequency halves the size element which may be resolved, i.e., doubles the resolution. Yet the size of the aperture, hence, the number of x-ray photons received remains the same. Thus, the noise level remains substantially the same while the resolution is substantially doubled.

Further, for some applications it may be desirable to weight two or more separated areas of the beam more heavily. For example, the spatial response may be described as a generally bell-shaped curve with a dimple at the apex. Yet, other spatial responses such as a truncated triangular wave, curves 16 or 18, or the like may be employed. This small alteration in the wave form may provide improved edge enhancement or other benefits in the reconstructed image.

Other spatial distributions can be used to weight part of the beam more heavily. Curve 14 illustrates bell-shaped spatial response which by similar analyses can be shown to have a spatial frequency of 1/A. An advantage of a generally bell-shaped spatial response is that the modulation transfer function is also a bell-shaped distribution as shown by curve 14 in FIG. 3. The bell-shaped modulation transfer function 14' approaches the first zero of the spatial frequency 1/A asymptotically, whereas modulation transfer functions 10' and 12' are generally sinusoidally damped The photoelectric means, such as photomultiplier tubes, photodiodes, or the like, produces an electrical signal whose amplitude is proportional to the amount of light received from the luminescence means. Variations in the intensity of the light produce corresponding variations in the amplitude of the electrical signal. The area of the luminescence means at the first, more responsive segment of the detector width produces a greater intensity of light from a given number of radiation photons than are as adjacent less responsive segments. For the responses illustrated in curves 12, 14, 16 and 18 the first more responsive segment is centrally located relative to the width and the less sensitive areas are peripherally located relative to the width.

In examining a planar slice, the beam of radiation has a finite width. A relatively dense incremental element which is small in comparison to the width of the beam will cast a shadow on part of the detector when it is in the path of the beam. More accurately, the incremental element absorbs some photons of the radiation producing a shadow of a reduced number of photons. If the shadow is cast on the central, more responsive segment of the detector width, a relatively large reduction in the amplitude of the electrical signal results. If the shadow is cast on the peripheral, less responsive segment, a relatively small reduction in the amplitude of the electrical signal results. In this manner, variations in the electrical signal are affected more greatly by incremental elements in the central part of the beam than by incremental elements in a peripheral part of the beam. Thus, the detector weights the response in favor of radiation impinging on the more responsive segment of its width.

The invention may be implemented with numerous physical embodiments. FIG. 1 illustrates a computerized tomographic scanner A with radiation detectors in accordance with the present invention. A rotating fan-beam type scanner is illustrated, however it should be appreciated that the present invention is equally applicable to traverse and rotate and other types of scanners.

The scanner comprises a tubular element 30 which functions to support a patient 32 or other object to be examined. The source of radiation C is mounted for rotational movement about element 30. The source comprises an x-ray tube 34 and a shutter mechanism 36 for defining a continuous swath of radiation diverging from substantially a point source. The shutter mechanism may be adjustable for selecting different size scan circles and different thicknesses of patient slices for examination. Alternately, the shutter mechanism may divide the radiation swath into a plurality of narrow, discrete beams. A reference detector 38 measures the intensity of the radiation before it traverses the scan circle. A means 40 rotates the source of radiation and provides an indication of the angular orientation of the source relative to the scan circle.

The radiation detector means D may take several forms as illustrated below. The detector means may comprise an arc of detectors which rotate with the source of radiation. The arc is defined by the maximum fan beam of radiation. The detector means may comprise an arc of stationarily mounted detectors. The stationary detectors may span an arc 42-44 defined in phantom or may circumscribe the scan circle. A support structure with small flanges such as 46 slightly overlaying the responsive surface of the detectors holds the detectors in place. The spacing between adjacent flanges determines the beam width. An exemplory beam 48 in the continuous fan-shaped swath of radiation has a width 50.

The detector means D and reference detector 38 are connected to a comparator 52 of processing means E. The comparator 52 compares the intensity of radiation before and after traversing the scan circle. The comparator provides a processor 54 with a series of indications of the logarithm of the radiation attenuation along various paths through the scan circle. Processor 54 operates on the data with conventional algorithms to produce an electronic representation of the tomographic image for display on video monitor 56. A suitable processor is described in co-pending application Ser. No. 838,084 filed Sept. 30, 1977, the disclosure of which is incorporated herein by reference.

A preferred embodiment of a detector from detector means D is illustrated in FIG. 4. The detector comprises luminescence means F and photoelectric means G which are optically coupled by coupling means H. The luminescence means comprises a first or central scintillation crystal means 60, such as a crystal of cadmium tungstate or calcium tungstate. The central scintillation crystal means has a configuration of a solid figure, preferably a rectangular prism. The solid figure has two oppositely disposed planar faces. A second scintillation crystal means comprises a pair of crystals 62 and 64 oppositely disposed adjacent the central scintillation. Crystals 62 and 64 have the configurations of solid figures, each having a generally planar face disposed adjacent to and parallel with one of the generally planar faces of central scintillation crystal means. In the preferred embodiment, these solid figures are also rectangular prisms. The pair of scintillation crystals 62 and 64 may be bismuth germanate (BGO). The generally planar faces of the rectangular prisms are oriented generally perpendicular to the width of first dimension and generally parallel to the received radiation. This provides a non-constant spatial response across the planar faces along the width.

Cadmium tungstate produces essentially the same number of scintillations as BGO from a given number of photons of x-rays. However, the cadmium tungstate scintillations are brighter than the BGO scintillations. Thus, the cadmium tungstate generates a greater intensity of light than BGO from the same number of photons of incident radiation. The spatial response of the detector is describable by curve 18 of FIG. 2C. BGO generates blue light and cadmium tungstate generates a yellow-orange light. Silicon photodiodes are generally more sensitive to light in red range than to blue light. Thus, to photodiodes light from cadmium tungstate has the effect of light with a greater intensity than a like intensity of blue light. Photomultiplier tubes on the other hand, are generally more sensitive to light in the blue range. Various combinations of crystals may be selected. The crystal to be placed adjacent the segment(s) of the width to be weighted most heavily should have the higher conversion efficiency or best match to the spectrum of the photoelectric means. Table 1 provides a list of some suitable crystals with the peak emission and conversion efficiency characteristics.

| MATERIAL | WAVELENGTH OF MAXIMUM EMISSION (nm) | SCINTILLATION CONVERSION EFFICIENCY* |
|---|---|---|
| NaI(Tl) | 410 | 100 |
| CaF$_2$(Eu) | 435 | 50 |
| CsI(Na) | 420 | 85 |
| $\epsilon$LiI(Eu) | 470–485 | 35 |
| TlCl(BeI) | 465 | 2.5 |
| CsF | 390 | 5 |
| BaF$_2$ | 325 | 10 |
| Bi$_4$Ge$_3$O$_{12}$ | 480 | 8 |
| KI(Tl) | 426 | 24 |
| CaWO$_4$ | 430 | 50 |
| CdWO$_4$ | 530 | 65 |

*As a percent of the conversion efficiency of NaI(Tl)

Alternately, the luminescence means may be a doped scintillation crystal, such as NaI(Tl) with a spatially varient density of doping material along its width such as by ion implanting.

The optical coupling means H is a section of LUCITE shaped at one end to match the luminescence means and shaped at the other to match the light sensitive area of the photoelectric means. The photoelectric means G may be a photomultiplier tube such as a Hamamatsu photomultiplier tube Model No. R-647. Alternately, the photoelectric means may be a photodiode, as illustrated in U.S. Pat. No. 4,070,581, issued Jan. 24, 1978.

FIGS. 5A, 5B and 5C show an alternate embodiment of a radiation detector in which the luminescence means produces the non-constant spatial response of the detector. Like elements in FIGS. 5A, B and C are marked with the same reference numeral as corresponding elements in FIG. 4 followed by a prime ('). Radiation impinges on a top face 66 of the luminescence means. The luminescence means comprises a central scintillation crystal means 60' surrounded by a second scintillation crystal means 62' adjacent the first more response segment of the detector width. As shown in FIG. 5B, the central scintillation crystal means may have the configuration of a solid figure with a convex arcuate face such as a cylinder. The second scintillation crystal means may have a configuration of a solid figure with a concave arcuate face disposed adjacent the convex arcuate face such as a surrounding tube. Unlike the embodiment of FIG. 4 which had a non-constant spatial response in only one dimension, the embodiment of FIG. 5B has the same non-constant spatial response in two dimensions. The embodiment of FIG. 5B is ideally suited for x-y flaw detectors and patterns. Alternately, as shown in FIG. 5C, the central scintillation crystal means may be a generally rectangular prism and the second scintillation means a generally rectangular surrounding tube. This provides improved resolution in the width and thickness dimensions for radiation beams of the thickness of the full crystal thickness. However, beams of a lesser thickness have improved resolution only in the width dimension.

A radiation permeable but light impermeable coating 68, such as black plastic or paint encases the luminescence means and the optical coupling means to prevent stray light for causing false signals. Optical coupling means H may be a conventional optical coupling cement.

FIG. 6 shows another alternate embodiment of a radiation detector in which the luminescence means produces the non-constant spatial response of detector. Like elements in FIG. 6 are marked with the same reference numerals as corresponding elements in FIGS. 4 and 5 followed by a double prime ("). Radiation impinges along the width of top face 66". The luminescence means comprises a scintillation crystal means 70. Preferably, the scintillation crystal is a single crystal of BGO, although means 70 may be other scintillation crystals. The luminescence means further comprises a covering means having a first part 72 and a second part 74. The first part has a light reflective surface disposed at the segment of detector width that is to be weighted more heavily. The second part 74 has a less reflective surface disposed adjacent the part or parts of the scintillation crystal means that are at segments of the width to be weighted less heavily. The first part is a thin polished metallic foil and the second part is black paint. A coating 68" may encase the covering means.

FIG. 7 illustrates a top view from the perspective of the radiation source of yet another embodiment of a radiation detector in which the luminescence means produces the non-constant spatial response of the detector. The luminescence means F has a non-constant cross-section transverse to the beam which rougly corresponds to the non-constant spatial response of the detector. The luminescence means comprises a scintillation crystal means having the configuration of a solid figure. The solid figure has a generally planar top surface 80 and a generally planar bottom surface disposed generally parallel to the top surface; the top and bottom surfaces having generally T-shaped profiles. The top surface spans the width of the detector and the maximum thickness of the x-ray beam. The greater amount of crystal adjacent the central section of the photoelectric means G and the lesser amount of crystal adjacent the periphery of the width causes a non-linear spatial response weighted more heavily toward the center. Each T-shaped face is oppositely disposed from the T-shaped face of the adjacent detectors. The T-shaped detectors mesh to form a linear array. Adjacent the crystals are optically isolated. Further, the symmetry relative to the thickness dimension 82 allows the shutter 36 to contract the beam thickness without altering spatial response. Alternately, the luminescence means may have other cross-sections such as triangular, sinusoidal, or various other meshing or interlocking configurations. Further, the luminescence means may comprise a scintillation means comprising a plurality of optically coupled crystals.

FIG. 8 shows another embodiment in which the luminescence means produces the non-constant spatial response of the detector. Like elements in FIG. 8 are marked with the same reference numerals as FIGS. 4 through 6, followed by a triple prime ('''). The luminescence means comprises first and second scintillation crystal means. The second scintillation crystal means comprises a BGO scintillation crystal 62''' having a slot cut transverse to its width. Crystal 62''' is relatively thick adjacent the less responsive segments of the detector width and has relatively thin bridge 90 adjacent the more responsive segment of the detector width. The first scintillation crystal means comprises a cadmium tungstate scintillation crystal 60''' disposed in the slot of crystal 62'''. Crystal 60''' and bridge 90 of crystal 62''' are disposed adjacent the first more sensitive segment of the detector width.

There is a tendency for x-rays of a higher energy to penetrate deeper into a scintillation crystal before producing a scintillation than x-rays of a lower energy. Accordingly, the scintillations produced in crystal 60''' are produced primarily in response to relatively low energy photons and the scintillations in bridge 90 are produced in response to relatively high energy photons. This non-constant responsiveness along the path of the radiation beam produces a non-constant energy or spectral response of the detector. Particularly, lower energy x-ray photons tend to produce a higher intensity of light than high energy x-ray photons.

The division between higher and lower energy x-ray photons is selected by selecting the dimension of crystal 60''' in the direction of x-ray travel. The non-constant spectral response can also be created adjacent the less responsive segments of the detector. A suitable construction is six crystals stacked two deep across the width of the detector. By selecting crystals with two or three conversion efficiencies and by selecting the depth of each crystal, various non-constant spatial and spectral responses can be achieved. If the higher energy photons are to be weighted more heavily, the crystal with the lower conversion efficiency is placed on the top of the crystal with the higher conversion efficiency on the bottom. To emphasize a middle energy range, a sandwich of three or more crystals may be employed. The invention further includes detectors with a constant spatial and non-constant spectral response.

Alternatively, the optical coupling means can be constructed to produce the non-constant spatial response of the detector. FIG. 2A illustrates such an embodiment. A scintillation crystal means 100, such as a single crystal of BGO, receives incident radiation and generates light of a constant intensity across the width of the detector. A coating means 102 such as metallic foil prevents stray light from causing false signals and reflects light back into crystal 100 to increase the intensity. The optical coupling means H comprises a filter means 104. The filter transmits a greater intensity of the light produced in response to radiation received at the segment of the width to be weighted most heavily. The filter means may vary in opacity, index of refraction, color, reflectivity or the like. An optical coupling grease may be employed to couple the filter means with the luminescence means and the photoelectric means. Alternately, the optical coupling means may comprise diverging and converging light pipe to redistribute the light from the luminescence means.

Alternately, the photoelectric means can be constructed to produce the non-constant spatial detector response of the detector. FIG. 9 illustrates such an embodiment. The luminescence means F comprises a first scintillation crystal means 110. The first crystal means comprises three laminar crystals. The luminescence means further comprises second scintillation crystal means 112 and 114 adjacent the first scintillation crystal means. The photoelectric means comprises a first photoelectric transducer means 116 adjacent the first scintillation crystal means and second photoelectric transducer means 118 and 120 adjacent the second scintillation crystal means 112 and 114 respectively. The first scintillation crystal means generates a greater intensity of light than the second scintillation crystal means. Alternatively, the luminescence means may be a single crystal and the first photoelectric transducer means may be more sensitive to the light generated than the second photoelectric means. In the preferred embodiment, the first and second photoelectric transducer means are photodiodes. The photodiode 116 adjacent the first scintillation crystal means is connected to one input of a differential amplifier 122. Photodiodes 118 and 120 disposed adjacent the second scintillation crystal means are connected with a second input of the differential amplifier. This produces a response as illustrated by curve 16 of FIG. 2C.

Alternately, scintillation crystal 112 and photodiode 118 may be replaced with a first solid state or ionization detector; scintillation crystals 110 and photodiode 116 may be replaced with a second solid state or ionization detector; and scintillation crystal 114 and photodiode 120 may be replaced with a third solid state or ionization detector. One of the solid state or ionization detectors, e.g., the center detector, may be selected to have a greater sensitivity to the incident radiation than the other two.

FIG. 10 shows another alternate embodiment in which the photoelectric means produces the non-constant spatial response. Like elements in FIG. 10 are marked with the same reference numerals as FIG. 9 followed by a prime ('). The luminescence means F comprises first scintillation crystal means 110' and second scintillation crystal means comprising crystals 112' and 114' flanking the first scintillation crystal means. The photoelectric means comprises a first photoelectric transducer means 116' adjacent the first scintillation crystal means and second photoelectric transducer means comprising transducers 118' and 120' adjacent crystals 112' and 114' respectively. Connected with photoelectric means is a means 124 for determining the rate of change of the intensity of radiation received by the detector. In the preferred embodiment, this rate of change means comprises a comparator for comparing the amount of radiation received by crystals 112' and 114'. As the radiation path moves relative to the patient, the radiation impinging on crystals 112' and 114' is substantially the same when the rate of change is low. But when the radiation path moves through parts of the patient which cause sudden changes in the intensity of radiation passing through the patient, the outputs of transducers 118' and 120' become unbalanced. When comparator 124 detects a state of unbalance, it causes the input of differential amplifier 122' from transducers 118' and 120' to be reduced by attenuator means 125. Means 125 may be a variable resistor, or the like, which attenuates the signals from transducers 118' and 120' to a greater or lesser degree as the comparator 124 becomes more or less unbalanced respectively. Attenuating means 125 may alternately be a switch which totally cuts off the signals from transducers 118' and 120' when the comparator becomes unbalanced. In this manner, the effective size of the detector is decreased when the radiation intensity traversing the patient varies rapidly with spatial movement of the radiation path and is increased when the radiation intensity varies slowly.

Figure 11:
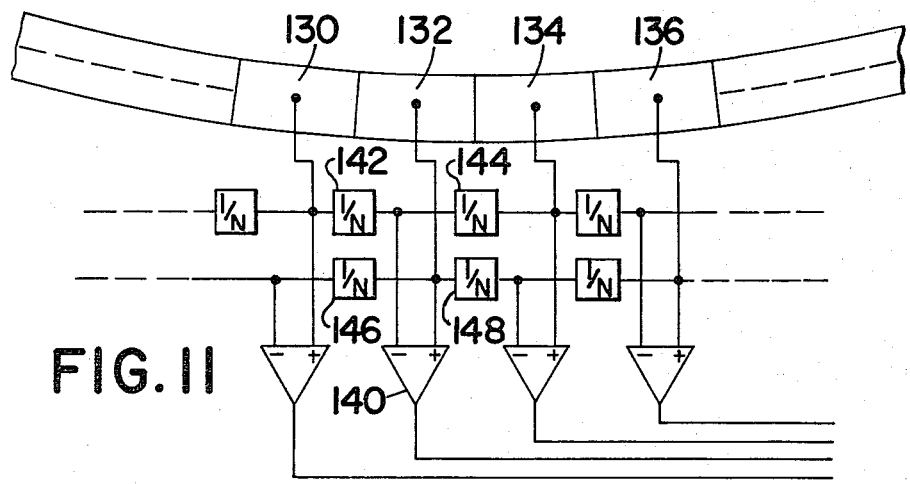
FIG. 11 illustrates an alternate embodiment of detector means in accordance with the present invention.

FIG. 11 illustrates another detector means having a non-constant spatial response. The detector means comprises a plurality of detectors such as ionization chambers and an electronic means for altering the signals of each of the detectors with the electrical signals from at least one other detector. Four of the detectors 130, 132, 134 and 136 are illustrated. Detector 132, for example, is connected with one input of a combining means 140. Another input of the combining means is connected with means 142 for altering the amplitude of the electrical signal from adjacent detector 130 and with means 144 for altering the amplitude of the electrical signal from detector 134. Means 142 and 144 in the preferred embodiment are means for reducing the amplitudes, such as a series connected resistor and diode. Detector 132 is also connected with means 146 and 148 for reducing the amplitude of the electrical signals from detector 132 and supplying the reduced signals to combining means associated with detectors 130 and 134. In the preferred embodiment, the combining means are differential amplifiers for substractively combining each signal with the reduced signals. Rather than reducing the amplitude of the electrical signals from the adjoining detectors, the signal from each detector can be increased and combined with the signals from adjoining detectors. The combining means and altering means comprise the electronic means for altering the signals. The detectors may also be solid state detectors, scintillation crystal-photoelectric detectors, one of the preceding detectors, or the like.

Figure 12:
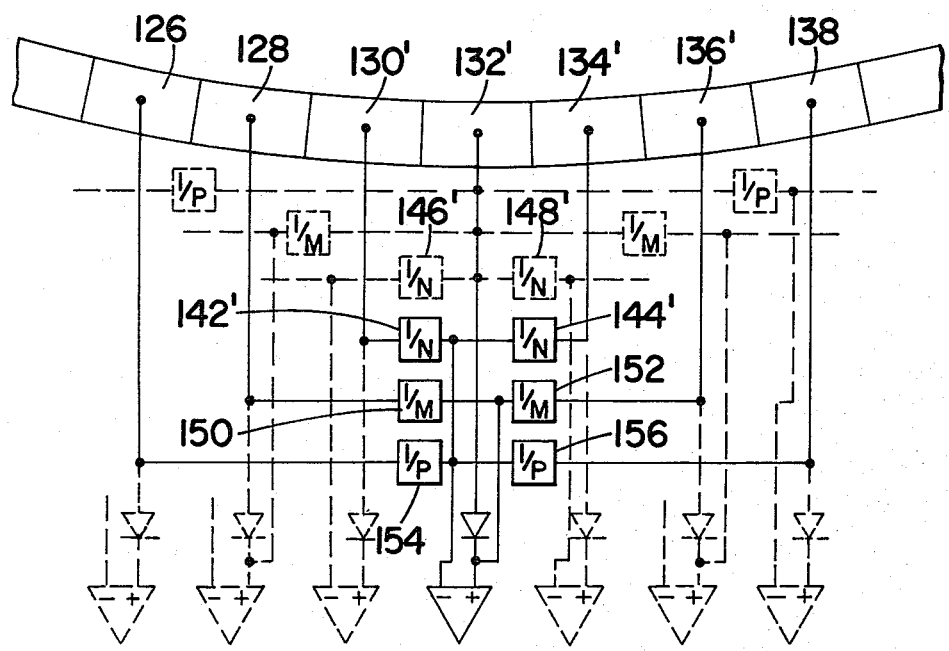
FIG. 12 illustrates an alternate embodiment of the detector means of FIG. 11.

FIG. 12 is an alternate embodiment of the detector means of FIG. 11. Like elements in FIG. 12 are marked with the same reference numerals as corresponding elements in FIG. 11 followed by a prime ('). The detector means comprises a plurality of adjacent detectors connected with a convolution means. The convolution means is analogous to the electronic altering means of FIG. 10 except that it alters the signals from each detector with the signals from an arc segment of detectors. The number of detectors which contribute to the alteration is determined by the convolution function chosen. A common convolution function subtracts a fraction of the adjoining detectors signal, adds a smaller fraction of the next adjoining detectors, subtracts a still smaller fraction of the next closest detectors, etc. FIG. 11 illustrates this convolution function, but other functions, such as those which skip some closer detectors and add or subtract components of some further detectors, may be similarly implemented. For simplicity of illustration, only the components which are combined with to the electrical signal of detector 132 are illustrated. The components which contribute fractional parts of the signal from detector 132 to adjust other detector signals are shown in phantom. Altering means 142' and 144' reduce the electric signals from detectors 130' and 134' and supply them to the inverting input of a combining means 140'. Altering means 150 and 152 reduce the electric signals from detectors 128 and 136'. The reduced signals from reducing means 150 and 152 are supplied to the non-inverting input of combining means 140'. Altering means 154 and 156 reduce the electric signals from detectors 126 and 128 and supply the reduced signals to the inverting input of combining means 140'. Further, altering means may contribute fractional parts of the electric signals from other detectors. In the preferred embodiment, altering means 154 and 156 reduce the signal more than altering means 150 and 152 which in turn reduce the signals more than altering means 142 and 144'. The detectors may be ionization chambers, solid state detectors, scintillation crystal-photodiode or photomultiplier tube detectors, one of the detectors of FIGS. 2-9, or the like.

The invention has been described with reference to preferred and alternate embodiments. Obviously, modifications and alterations will occur to others upon reading and understanding this specification. The features of several embodiments may be combined in full or in part. Such combinations may produce more smoothly varying or more elaborate non-constant spatial or spectral responses or combinations of one or two dimensional spatial and spectral responses. It is my intention to include all such modifications, alterations and combinations insofar as they come within the scope of the appended claims or their equivalents.

I claim:

1. A computerized tomographic scanning apparatus for examining a planar slice of an object in the plane of a scan circle with radiation and producing a representation of an image of the planar slice, comprising:

at least one source of radiation for producing at least a beam of radiation in the plane of said scan circle;

radiation detector means for producing electrical signals in response to received radiation, said detector means disposed to receive radiation from the source which has traversed the scan circle, said detector means having a non-constant spatial response in at least a first dimension in the plane of the scan circle; and processing means for processing the electrical signals from the detector means to produce the representation of an image.

2. The apparatus as set forth in claim 1 wherein said detector means comprises at least one detector, said detector having a non-constant spatial response along said one direction, the detector being more responsive to radiation received along a first segment of the detector than to radiation received along at least a second segment of the detector, said second segment disposed adjacent the first segment along the first dimension, whereby the detector weights radiation received adjacent the first segment more heavily than radiation received along the second segment.

3. The apparatus as set forth in claim 2 wherein said first segment is centrally disposed on the detector relative to said first dimension and said second segment is peripherally disposed on the detector relative to said first dimension, whereby the detector weights the radiation received adjacent the center of the detector more heavily than radiation received adjacent the edges.

4. The apparatus as set forth in claim 3 wherein the non-constant spatial response of the detector is characterized by a generally bell-shaped function in which the bell-shaped function is generally centered relative to the first dimension of the detector.

5. The apparatus as set forth in claim 2 wherein said detector comprises a luminescence means for transforming the received radiation to light, said luminescence means transforming radiation received adjacent the first segment of the detector into light of a greater intensity than radiation received adjacent the second segment of the detector; and photoelectric means for producing the electrical signals in response to light received, said photoelectric means being optically coupled with said luminescence means; whereby the electrical signal is indicative of a weighted sum or average of the amount of the radiation received adjacent the first and second segments with the radiation received adjacent the first segment being weighted more heavily.

6. The apparatus as set forth in claim 5 wherein said luminescence means comprises a first scintillation crystal means comprises a first scintillation crystal means at the first segment and a second scintillation crystal means at the second segment, said first scintillation crystal means converting a predetermined amount of radiation into a greater intensity of light than said second scintillation crystal means.

7. The apparatus as set forth in claim 6 wherein said first scintillation means is cadmium tungstate and said second scintillation means is bismuth germanium oxide.

8. The apparatus as set forth in claim 6 wherein said first scintillation crystal means is a first prism and said second scintillation crystal means is a pair of prisms, the prisms of said pair of prisms are disposed adjacent generally opposing sides of said first prism whereby the radiation received by the first prism is weighted more heavily than the radiation received by the pair of prisms.

9. The apparatus as set forth in claim 8 wherein said second scintillation crystal means further compries a bridge prism connecting said pair of prisms whereby a said second scintillation crystal means forms a solid figure having a generally rectangular trough for receiving at least part of said first prism.

10. The apparatus as set forth in claim 5 wherein said luminescence means comprises a scintillation crystal means and covering means for covering at least a part of the scintillation crystal means, the covering means comprising a first part having a light reflective surface disposed adjacent the scintillation crystal means at said first segment, and a second part having a less light reflective surface than the first part disposed adjacent the scintillation crystal means at said second segment, whereby the reflective surface of the first part increases the intensity of light from an adjacent part of the scintillation crystal means.

11. The apparatus as set forth in claim 10 wherein said first part of the covering means comprises a thin polished metallic strip oriented generally traverse to the first dimension of the detector.

12. The apparatus as set forth in claim 5 wherein said luminescence means comprises a scintillation crystal means having a configuration of a solid figure, said solid figure having a first and second generally planar face, said second generally planar face being disposed oppositely from and generally parallel to said first generally planar face, said first and second generally planar faces having generally T-shaped profiles.

13. The apparatus as set forth in claim 12 wherein said first generally planar face is disposed generally perpendicular to the plane of said scan circle and generally parallel to said first dimension.

14. The apparatus as set forth in claim 13 wherein said detector means comprises a plurality of detectors, each of the plurality of detectors having a scintillation crystal means having a generally T-shaped face, each T-shaped face being oppositely disposed and meshing to form a generally linear array.

15. The apparatus as set forth in claim 2 wherein said detector comprises a luminescence means for transforming the received radiation to light, said luminescence means transforming radiation received adjacent the first segment into light having a first spectral distribution and radiation received adjacent a second segment into light having a second spectral distribution; and photoelectric means for receiving light from the luminescence means and producing the electrical signals in response to the received light, said photoelectric means being more responsive to the first spectral distribution whereby the electrical signals are weighted more heavily by the radiation received adjacent the first segment.

16. The apparatus as set forth in claim 2 wherein said detector comprises luminescence means for transforming the received radiation into light, photoelectric means for receiving light from the luminescence means and producing the electrical signals in response to the received light, and optical coupling means for transmitting light from the luminescence means to the photoelectric means, said optically coupling means transmitting light transformed from radiation received adjacent the first segment with a first intensity and transmitting light transformed from radiation received adjacent the second segment with a lesser intensity, whereby the electrical signals are indicative of the weighted sum or average of the amount of radiation received adjacent the first and second segments with the radiation received adjacent the first segment being weighted more heavily.

17. The apparatus as set forth in claim 16 wherein said optical coupling means comprises a filter having at least a first and second opacity for attenuating light transformed from radiation received adjacent the second segment more than light transformed from radiation received adjacent the first segment.

18. The apparatus as set forth in claim 2 wherein said detector comprises a luminescence means for transforming the received radiation to light, a first photodiode means optically coupled with said luminescence means and a second photodiode means optically coupled with said luminescence means, the first and second photodiode means producing the electrical signals.

19. The apparatus as set forth in claim 18 further including a differential amplifier, said differential amplifier operatively connected with the first and second photodiode means for subtractively combining electrical outputs therefrom to produce said electrical signals.

20. The apparatus as set forth in claim 19 wherein said luminescence means comprises a first scintillation crystal means optically coupled with said first photodiode and a second scintillation crystal means optically coupled with said second photodiode, said first scintillation crystal transforming a given amount of received radiation into light of a greater intensity than said second scintillation crystal means.

21. The apparatus as set forth in claim 18 further comprising means for determining the rate of change of radiation received by the detector, and attenuating means for selectively attenuating the output of said second photodiode means, said attenuating means being operatively connected with the second photodiode means and being controlled by said rate of change means.

22. The apparatus as set forth in claim 21 wherein sid attenuating means varies the attentuation generally proportionally to the rate of change determined by said rate of change means.

23. The apparatus as set forth in claim 21 wherein said second photodiode means comprises first and second transducers oppositely disposed adjacent said first photodiode means and said rate of change means comprises a comparator for comparing the output of said first and second transducers.

24. The apparatus as set forth in claim 1 wherein said detector means comprises a plurality of detectors disposed generally along said first dimension and electronic means for altering the electrical signals of one of said detectors with the electrical signals from at least one adjoining detector.

25. The apparatus as set forth in claim 24 wherein said electronic means comprises means for reducing the amplitude of signals from said at least one adjoining detector and means for combining the reduced electrical signals with the electrical signals from the one of said detectors.

26. The apparatus as set forth in claim 25 wherein said combining means is a differential amplifier whereby the reduced electrical signals are subtractively combined with the electrical signals from the one of said detectors.

27. The apparatus as set forth in claim 1 wherein said detector means comprises a plurality of detectors disposed generally along said first dimension, each of said plurality of detectors producing electrical signals in response to detected radiation and convolution means for additively and subtractively combining fractional parts of the electrical signals from at least some of said plurality of detectors with the electrical signals from at least one of the detectors, said convolver means being operatively connected with said plurality of detector means.

28. The apparatus as set forth in either one of claims 24 or 27 wherein each of said detectors comprises an ionization chamber.

29. The apparatus as set forth in either one of claims 24 or 27 wherein each of said detectors comprises a solid state radiation detector.

30. The apparatus as set forth in either one of claims 24 or 27 wherein each of said detectors comprises luminescence means for transforming received radiation into light and photoelectric means for producing electrical signals in response to light received from said luminescence means, said photoelectric means optically coupled with said luminescence means.

31. A computerized tomographic scanning apparatus for examining a planar slice of an object in the plane of a scan circle with radiation and producing a representation of an image of the planar slice, the apparatus comprising:
at least one radiation source for producing beams of radiation generally in the plane of the scan circle,
at least one radiation detector for producing electrical signals in response to received radiation, said radiation detector disposed to receive radiation from said source which has traversed the scan circle, said detector comprising a luminescence means for transforming received radiation into light and photoelectric means for producing the electrical signals in response to light from said luminescence means, said photoelectric means being optically coupled with said luminescence means, said luminescence means comprising a first scintillation crystal means and a second scintillation crystal means; and
processing means for processing the electrical signals from the detector to produce the representation of an image.

32. The apparatus as set forth in claim 31 wherein said first scintillation crystal means comprises a first solid figure having at least one generally planar face and wherein said second scintillation crystal means comprises a second solid figure having at least one generally planar face, said first and second crystal means disposed with said generally planar faces disposed adjacent to and generally parallel with each other.

33. The apparatus as set forth in claim 32 wherein said first scintillation crystal means is more responsive to received radiation than said second scintillation crystal means.

34. The apparatus as set forth in claim 33 wherein said generally planar faces are oriented generally perpendicular to the plane of the planar slice.

35. The apparatus as set forth in claim 34 wherein said faces are oriented generally parallel to a beam of received radiation whereby the detector has a non-constant spatial response across said generally planar faces.

36. The apparatus as set forth in claim 34 wherein said generally planar faces are oriented generally perpendicular to a beam of received radiation, whereby the detector has a non-constant spectral response to the energy of the received radiation.

37. The apparatus as set forth in claim 36 wherein said first scintillation crystal means is disposed substantively between said source and said second scintillation crystal means whereby the detector is more responsive to lower energies in the received radiation energy spectrum.

38. The apparatus as set forth in claim 33 wherein said first solid figure is a generally rectangular prism whereby said first solid figure has another generally planar face disposed opposite and generally parallel to its first generally planar face.

39. The apparatus as set forth in claim 38 wherei said second scintillation crystal means further comprises a third solid figure having a generally planar face, the generally planar face of said solid figure being disposed adjacent to and generally parallel with said another planar face of the generally rectangular prism.

40. The apparatus as set forth in claim 38 wherein said second solid figure is a generally a second rectangular prism having a generally rectangular trough in one face thereof, said rectangular prism being disposed at least partially in said trough.

41. The apparatus as set forth in claim 31 wherein said first scintillation crystal means comprises a first solid figure having at least a generally convex arcuate face and wherein said second scintillation crystal means comprises a second solid figure having a generally concave arcuate face, said first and second scintillation crystal means disposed with said convex arcuate faces adjacent said concave arcuate face.

42. A radiation detector comprising a scintillation crystal means for producing light in response to incident radiation and means for covering the scintillation crystal means, said covering means having a first part with a first light reflective surface adjacent the scintillation crystal means and a second part with a second surface adjacent the scintillation crystal means, said second surface being less light reflective than said first surface and photoelectric means for producing electrical signals in response to received light, said photoelectric means being optically coupled with said scintillation crystal means.

43. A computerized tomographic scanning apparatus for examining a planar slice of an object in the plane of a scan circle with radiation and producing a representation of an image of the planar slice, the apparatus comprising:
at least one source of radiation for producing at least a beam of radiation in the plane of said scan circle;
at least one radiation detector having at least a first segment and a second segment which is disposed adjacent the first segment along a first dimension in the plane of the scan circle, the first and second segments being disposed to receive the beam of radiation from said source, the detector producing electrical signals in response to radiation received along the first and second segments, the detector being more responsive to radiation received along the first segment than to radiation received along the second segment such that the detector has a non-constant spatial response in the first dimension, and such that the electrical signals are weighted in favor of radiation received along the first segment;
processing means for processing the electrical signals from the detector means to produce the image representation, whereby the non-constant spatial response causes the noise degradation of the representation to be consonant with the noise degradation achieved with a detector which has a width in the first dimension which is substantially the same as the width in the first dimension of the first and second segments together but causes the resolution of the image representation to approach the higher resolution achieved with a detector which has a width in the first dimension which is generally the width of the first segment.

44. A computerized tomographic scanning apparatus for examining a planar slice of an object in the plane of a scan circle with radiation and producing a representation of an image of the planar slice, the apparatus comprising:
at least one radiation source for producing beams of radiation generally in the plane of the scan circle,
at least one radiation detector for producing electrical signals in response to received radiation, said radiation detector disposed to receive radiation from said source which has traversed the scan circle, said detector comprising a first scintillation crystal means for transforming received radiation into light of a first color spectrum, the first scintillation crystal means having a first scintillation conversion efficiency, a second scintillation crystal means for transforming received radiation into light of a second color spectrum, the second scintillation crystal means having a second scintillation conversion efficiency, and a photoelectric means optically coupled with the first and second scintillation crystals for converting the light from the first and second scintillation crystal means into electrical signals, the photoelectric means being most responsive to light in a third color spectrum, at least one of said first color spectrum and said first scintillation conversion efficiency being different from said second color spectrum and said second scintillation conversion efficiency, respectively, such that said electric signals vary as a weighted sum or average of the amount of radiation received by the first and second scintillation crystal means, whereby the sum or average is weighted in favor of the radiation transformed by the scintillation crystal means which has the color spectrum with the better spectral match to the third color spectrum and in favor of the radiation transformed by the scintillation crystal means which has the higher scintillation conversion efficiency; and
processing means for processing the electrical signals from the detector which vary as the weighted sum or average of the amount of radiation received by the scintillation crystal means to produce the image representation.

45. A radiation detector having a non-constant spatial response comprising:
a luminescence means for producing light in response to incident radiation, the luminescence means including a plurality of scintillation crystals disposed contiguous with each other in an arrangement such that taken together they form a solid geometric figure whose ends are substantially polygonal and equal in size and shape and whose faces are substantially planar, said plurality of scintillation crystals including at least a first scintillation crystal which produces light having a first color spectrum and a second scintillation crystal which produces light having a second color spectrum, said first color spectrum being different from said second color spectrum;

photoelectric means for producing electric signals which vary in response to received light, the photoelectric means being more responsive to light of the first color spectrum than the second color spectrum; and optical coupling means for optically coupling the photoelectric means and the luminescence means.

46. The detector as set forth in claim 45 wherein the plurality of scintillation crystals comprises at least three scintillation crystals extending between the ends of the solid geometric figure.

47. The detector as set forth in claim 46 wherein each of the faces and ends of the solid figure are substantially rectangular.

48. The detector as set forth in claim 45 wherein the first scintillation crystal is a cadmium tungstate crystal and said second scintillation crystal is a bismuth germanate crystal.

49. A radiation detector having a non-constant spatial response comprising:

a luminescence means for producing light in response to incident radiation, the luminescence means including a plurality of scintillation crystal materials disposed contiguous with each other in an arrangement such that taken together they form a solid geometric figure whose ends are substantially polygonal and equal in size and shape and whose faces are substantially planar, said plurality of scintillation crystal materials including at least a first scintillation crystal material which has a first scintillation conversion efficiency and a second scintillation crystal material which has a second scintillation conversion efficiency, the first and second conversion efficiencies being different;

photoelectric means for producing electric signals which vary in response to received light; and optical coupling means for optically coupling the photoelectric means and the luminesence means, whereby the electric signals vary with the aggregate of the light from the plurality of scintillation crystal materials.

50. A radiation detector comprising:

luminescence means for producing light in response to incident radiation;

at least first, second, and third photodiode means for producing electrical signals in response to light, said first, second, and third photodiode means being optically connected with said luminescence means; and combining means for combining the electrical signals from the second photodiode with a function of the sum of the electrcal signals from the first and third photodiode means to produce a combined electric signal, the combined electric signal representing a weighted sum or average of the amount of radiation responsive light detected by the three photodiode means.

51. The detector as set forth in claim 50 wherein the combining means includes a differential amplifier, whereby the electrical signals from the first and third photodiode means are subtractively combined with the electrical signals from the second photodiode means.

52. The detector as set forth in claim 50 wherein said luminescence means includes a first scintillation crystal optically coupled with the first photodiode means, a second scintillation crystal optically coupled with said second photodiode means and a third scintillation crystal being optically connected with said third photodiode means, said first and third scintillation crystals being disposed adjacent said second scintillation crystal.

53. A radiation detector comprising a luminescence means for producing light in response to incident radiation, said luminescence means having a radiation receiving face defined by a length and a width upon which the incident radiation is received, said radiation receiving face being defined by a wider portion and by at least one narrower portion such that the wider portion has more radiation receiving area per unit length than the narrower portion; photoelectric means for producing electrical signals in response to received light, the photoelectric means being optically coupled with said luminescence means, whereby variations in the amount of radiation received along the length of the radiation receiving face adjacent the wider portion cause greater variations in the electrical signals than variations in the amount of radiation receiving along the length adjacent the narrower portion.

54. The radiation detector as set forth in claim 53 wherein the radiation receiving face is defined by one wider portion disposed between two narrower portions such that the radiation receiving face is generally T-shaped.

55. A radiation detector having a substantially planar radiation receiving face, the detector comprising:

a first scintillation crystal, a second scintillation crystal and a third scintillation crystal which are disposed contiguous with each other, each of the first, second, and third scintillation crystals having a face which is disposed substantially contiguous with the planar radiation receiving face, the first and third scintillation crystals being bismuth germanate and the second scintillation crystal being cadmium tungstate;

a photoelectric means for producing electrical signals in response to received light; and optical coupling means for optically coupling the first, second, and third scintillation crystals with the photoelectric means.

* * * * *